US00PP36524P2

(12) United States Plant Patent
Whitehead

(10) Patent No.: US PP36,524 P2
(45) Date of Patent: Mar. 4, 2025

(54) ***CHIONANTHUS* TREE NAMED 'CVJMW'**

(50) Latin Name: *Chionanthus virginicus*
Varietal Denomination: CVJMW

(71) Applicant: HortSource LLC, Lincolnton, GA (US)

(72) Inventor: Dan Milton Whitehead, Lincolnton, GA (US)

(73) Assignee: HORTSOURCE LLC, Lincolnton, GA (US)

( * ) Notice: Subject to any disclaimer, the term of this patent is extended or adjusted under 35 U.S.C. 154(b) by 0 days.

(21) Appl. No.: 18/830,545

(22) Filed: Sep. 10, 2024

(51) Int. Cl.
*A01H 5/00* (2018.01)
*A01H 6/00* (2018.01)

(52) U.S. Cl.
USPC ..... Plt./216

(58) Field of Classification Search
USPC ..... Plt./216
See application file for complete search history.

*Primary Examiner* — Karen M Redden
(74) *Attorney, Agent, or Firm* — Penny J. Aguirre

(57) ABSTRACT

A new cultivar of *Chionanthus virginicus* tree named 'CVJMW' that is characterized by its prolific flowering; even as a young plant, its foliage that is dark green in color, its upright branching habit, its upright-oval form, and its vigorous growth rate.

4 Drawing Sheets

Botanical classification: *Chionanthus virginicus*.
Variety denomination: 'CVJMW'.

BACKGROUND OF THE INVENTION

The present invention relates to a new and distinct cultivar of *Chionanthus virginicus* and will be referred to hereafter by its cultivar name, 'CVJMW'. 'CVJMW' is a new fringe-tree tree grown for use as a landscape plant.

'CVJMW' was discovered by the Inventor as a chance seedling that was growing in a field plot planted with over 200 unnamed and unpatented plants of *Chionanthus virginicus* in Iva, South Carolina in June of 2021. The exact parentage is therefore unknown.

Asexual propagation of the new cultivar was first accomplished under the direction of the Inventor using stem cuttings in June 2021 in Rutledge, Georgia. Asexual propagation by stem cuttings has determined that the characteristics of the new cultivar are stable and are reproduced true to type in successive generations.

SUMMARY OF THE INVENTION

The following traits have been observed repeatedly and represent the characteristics of the new cultivar. These attributes in combination distinguish 'CVJMW' as a unique cultivar of *Chionanthus*.

1. 'CVJMW' exhibits prolific flowering, even as a young plant.
2. 'CVJMW' exhibits a compact plant habit with a dense canopy.
3. 'CVJMW' exhibits foliage that is dark green in color.
4. 'CVJMW' exhibits an upright branching habit.
5. 'CVJMW' exhibits an upright-oval form.
6. 'CVJMW' exhibits vigorous growth rate.

Plants of the species *Chionanthus virginicus* that were growing in the plot where the claimed plant was discovered, all differ from 'CVJMW' in having less vigorous growth habits, lighter colored foliage, less upright branch angles, and a less dense and less compact plant habit. 'CVJMW' can be most closely compared to the *Chionanthus virginicus* cultivars 'CVSTF' (Not Patented) and 'CV1049' (Not Patented). 'CVSTF' and 'CV1049' are both similar to 'CVJMW' in having a dense canopy and foliage that is dark green in color. 'CVSTF' differs from 'CVJMW' in having wider branch angles, a broader plant habit and leaves that are slightly longer and more broad. 'CV1049' differs from 'CVJMW' in having much wider branch angles, a rounded plant form and leaves that are wider.

BRIEF DESCRIPTION OF THE DRAWINGS

The accompanying colored photographs illustrate the overall appearance and distinct characteristics of the new cultivar of *Chionanthus*.

The photograph is FIG. 1 provides a view of 'CVJMW' in bloom.

Figure 1:
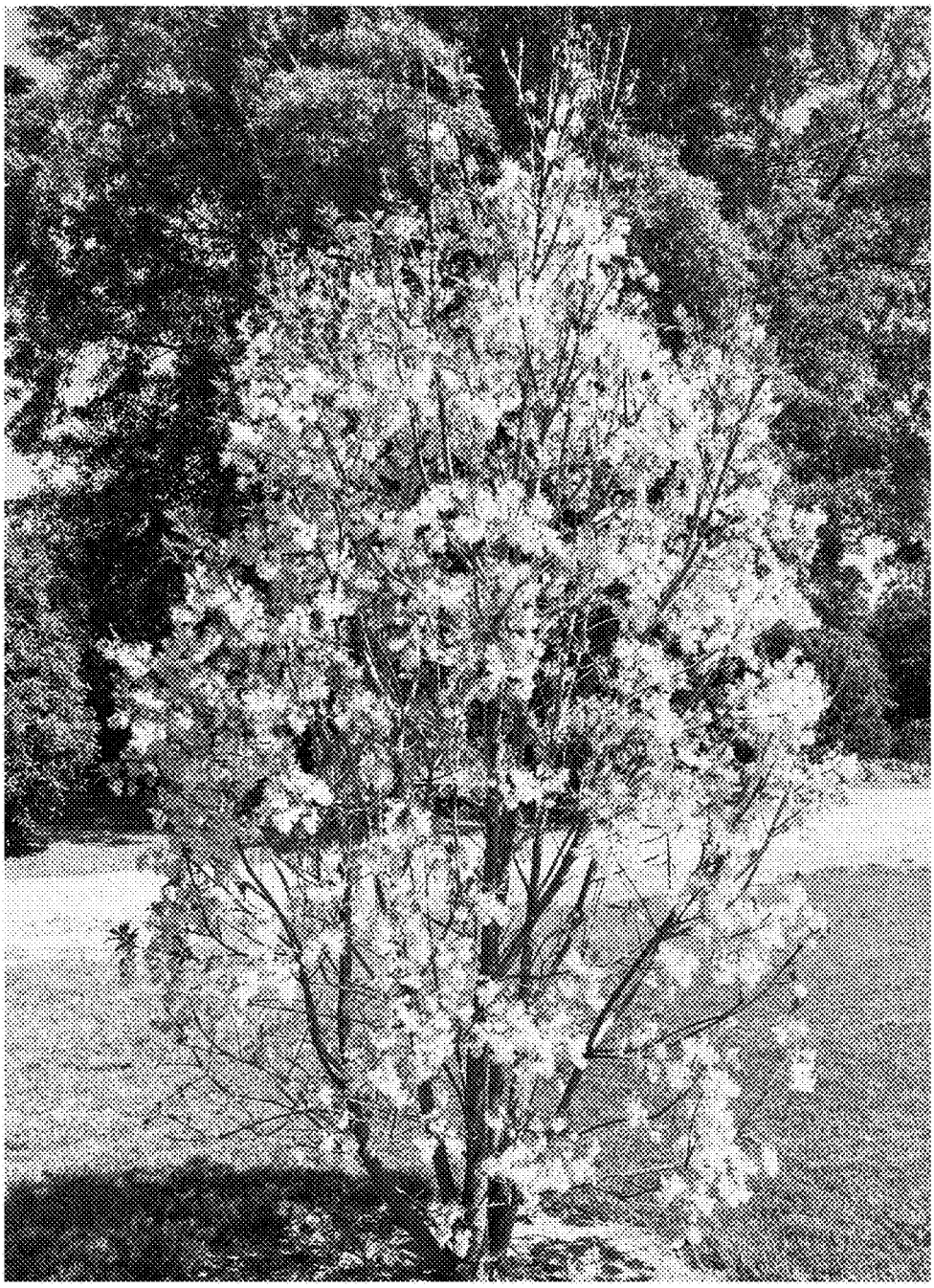
Figure 2:
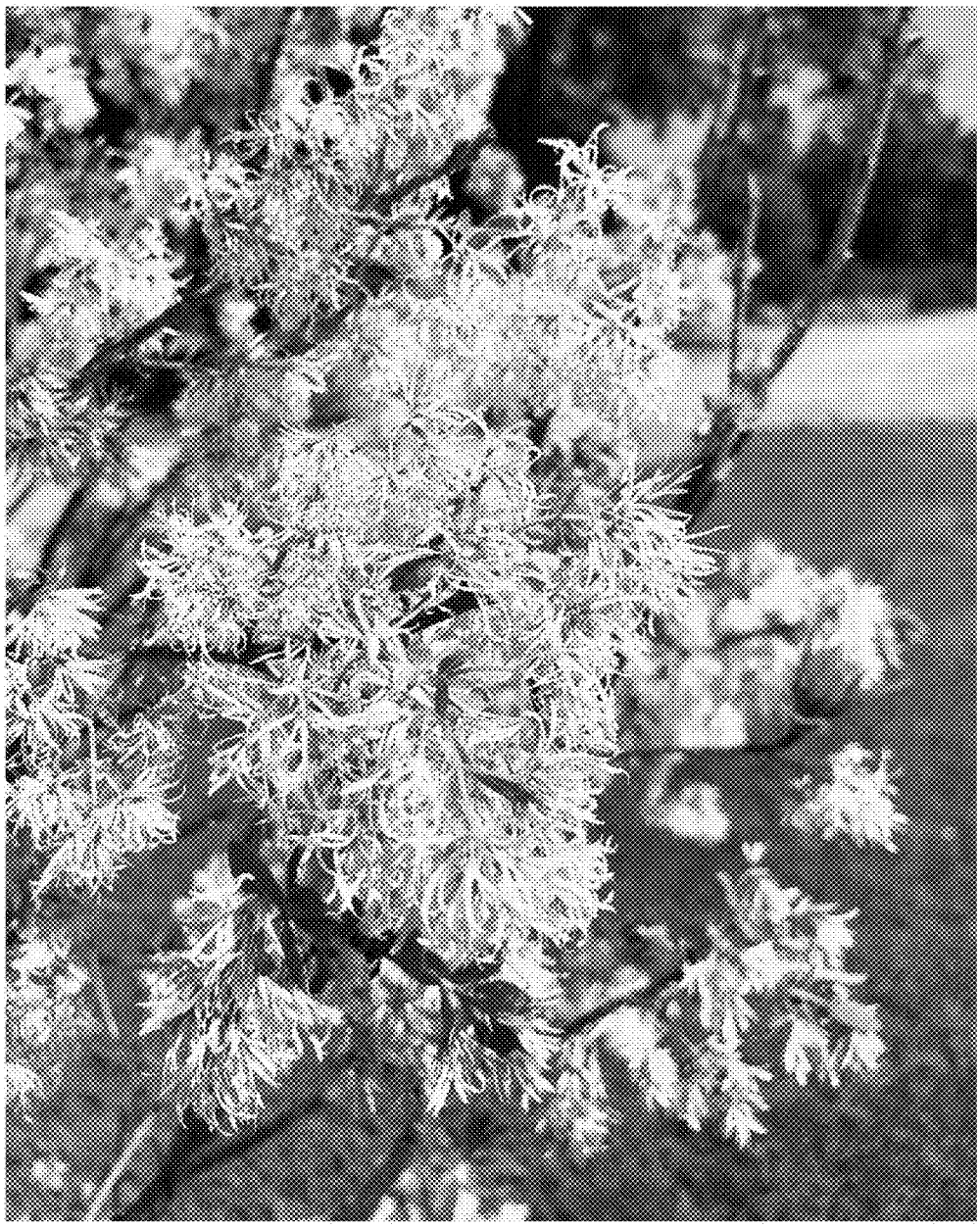

The photograph in FIG. 2 provides a close up view of the flowers.

Figure 3:
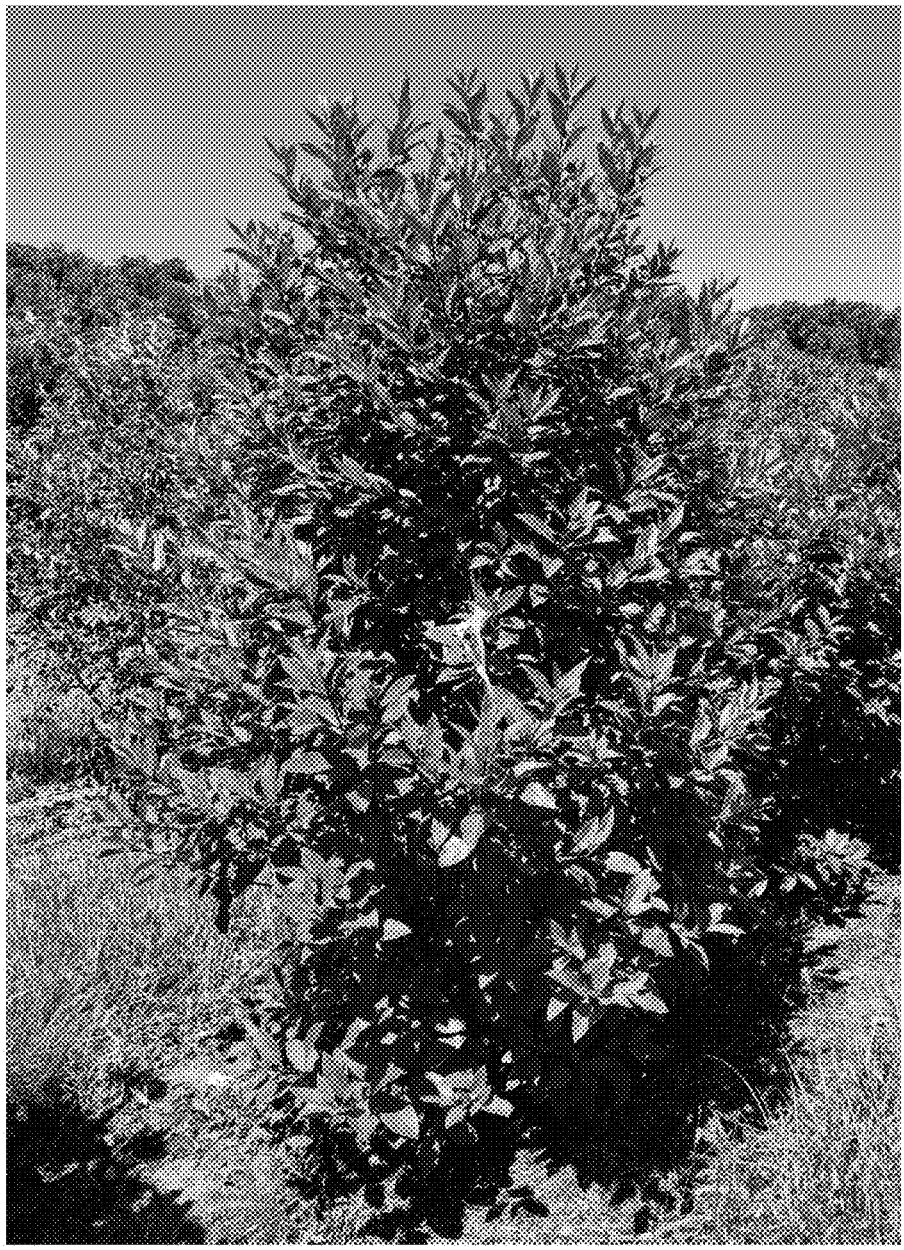

The plant in the photograph in FIG. 3 was taken of the 3-year-old tree originally grown in Iva, South Carolina showing a view of the foliage.

Figure 4:
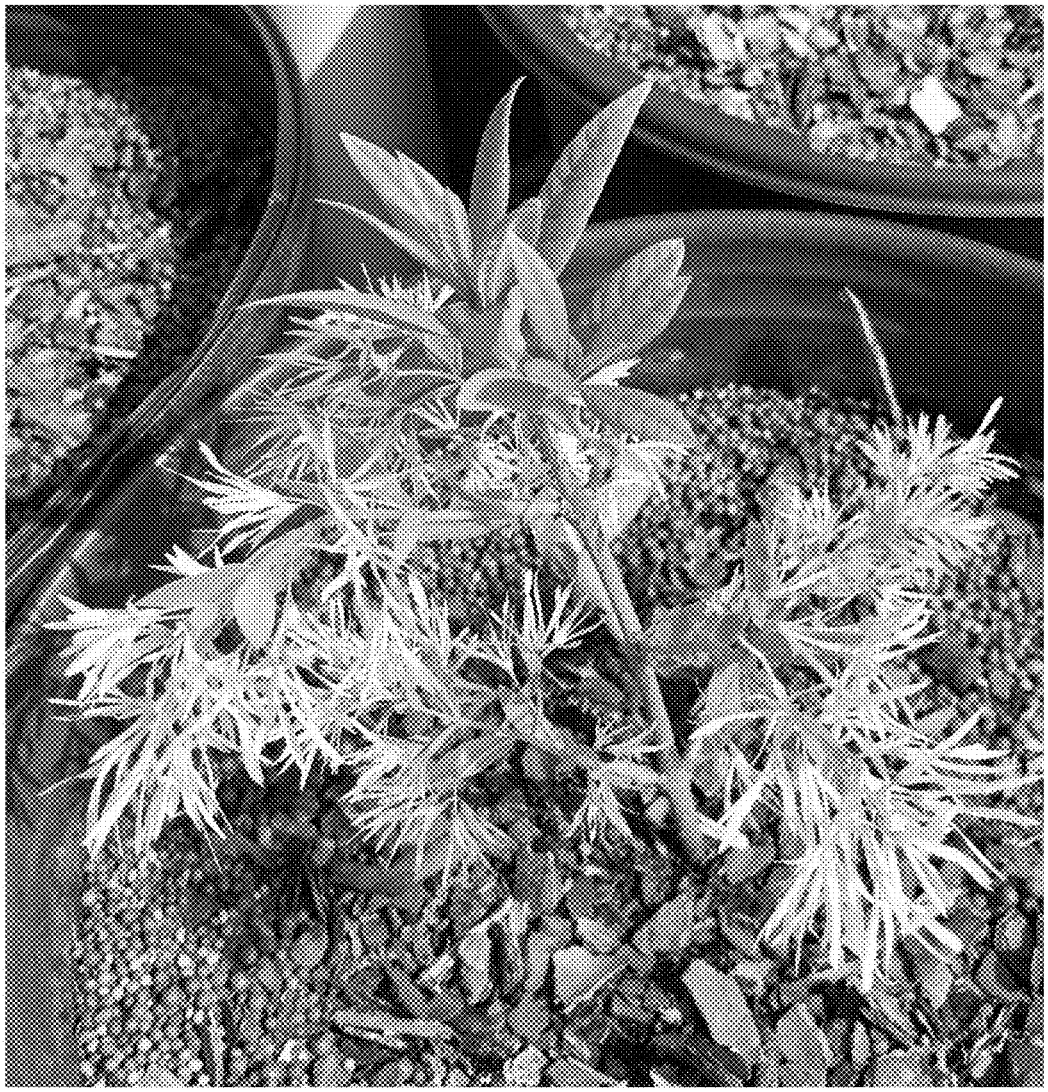

The photograph in FIG. 4 was taken of a plant about 9 months in age as grown outdoors in a 3-gallon container in Rutledge, Georgia and provides a view of the plant in flower at a very early age when grown in a container.

The colors in the photographs may differ slightly from the color values cited in the detailed botanical description, which accurately describe the colors of the new *Chionanthus*.

DETAILED BOTANICAL DESCRIPTION

The following is a detailed description of plants of the new cultivar grown outdoors in field production (3-years in age) and 3-gallon containers (9-months in age) in Rutledge, Georgia with other data collected from a plant about 5 years in age as grown in the ground in Rutledge, Georgia. The phenotype of the new cultivar may vary with variations in environmental, climatic, and cultural conditions, as it has not been tested under all possible environmental conditions. The color determination is in accordance with The 2001 Colour Chart of The Royal Horticultural Society, London, England, except where general color terms of ordinary dictionary significance are used.

General description:

*Blooming period*.—Early to mid-April depending on weather conditions in the Piedmont region of Georgia.

*Plant type*.—Deciduous flowering tree.

*Plant habit*.—Upright oval with a dense canopy.

*Height and spread*.—Reaches an average of 6 m in height and 4 m in spread as a mature plant in the landscape.

*Hardiness*.—At least in U.S.D.A Zones 5 to 9.

*Diseases and pests*.—No susceptibility or resistance to diseases or pests has been observed.

*Root description*.—Fibrous, freely branched and 165C in color.

*Propagation*.—Semi-hardwood stem cuttings.

*Root development*.—Cuttings root in about 35 days, about 12 months to produce a young plant from a rooted cutting.

*Growth rate*.—Moderate.

Branch description:

*Branch angles*.—Upper canopy branches more ascending, emerging at a 50° angle from main trunk, lower canopy averages 70° from trunk.

*Branch strength*.—Very strong.

*Branch size* (*as a* 5-*year-old tree*).—Trunk per multi-stem cane; average caliper 4.5 cm in diameter at 15 cm in height from the soil level, lateral branches; an average of 1.2 m in length and 2 cm to 2.5 cm in diameter.

*Branch surface*.—Smooth on younger branches becoming more textured with lenticels on mature bark; 200B in color, horizontal, an average of 1 cm in length, about 10 per trunk 8 cm by 8 cm.

*Branch color*.—Young emerging stems; 148A turning 147C, Trunk; 197C.

*Internode length*.—Average of 3.8 cm.

Foliage description:

*Leaf shape*.—Narrow elliptic to ovate.

*Leaf division*.—Simple.

*Leaf base*.—Cuneate.

*Leaf apex*.—Acute.

*Leaf fragrance*.—None.

*Leaf venation*.—Pinnate and reticulate, upper surface mid vein 151C, lower surface mid vein 145A, all other veins match leaf color.

*Leaf margins*.—Entire and slightly wavy as they mature.

*Leaf arrangement*.—Opposite.

*Leaf aspect*.—Held outward on pendant petioles, held in an average angle of 45° from branch.

*Leaf attachment*.—Petiolate.

*Leaf surface*.—Upper surface very glossy and leathery, lower surface matte and pubescent.

*Leaf size*.—Average of 13 cm in length, 6 cm in width.

*Leaf color*.—Young upper surface 144B, young lower surface N144CD mature upper surface 139A, mature lower surface 144A. Fall color is 163B.

*Petioles*.—Average of 1.5 cm in length, 1 mm in width, held at a 45° angle, smooth and glabrous surface, 151C in color.

Flower description:

*Inflorescence type*.—Dioecious pendant axillary panicles.

*Inflorescence size*.—10 to 12 cm in length and 6 cm in width.

*Flower type*.—Spreading and comprised of strap-like petals.

*Flower size*.—Average of 2 cm in length and width.

*Flower number*.—An average of 50 per inflorescence.

*Petals*.—4, linear in shape, 157B in color on both surfaces, average of 2 cm in length and 2 mm in width, entire margins, fused base, glabrous on both surfaces, pendulent in aspect.

*Sepals*.—4, fused into campanulate calyx, calyx about 2 mm in length and width, 144A in color.

*Peduncle*.—Primary; 10 cm in length and 3 mm in width, secondary; 1.5 cm in length and 2 mm in width, 145B in color, glabrous surface, strong.

*Pedicel*.—Average of 1.5 cm in length and 1.5 mm in width, glabrous surface, 144C in color, strong.

*Bracts*.—Average of 10 per inflorescence, leaf-like, primarily lanceolate in shape, glabrous on both surfaces, N137B to N137C in color on both surfaces, average of 3 cm in length and 1 cm in width.

*Flower fragrance*.—Slight, spicy.

*Flower longevity*.—Average of 10 to 14 days.

*Reproductive organs*.—Not observed.

*Fruit/seeds*.—Male, no fruit produced.

It is claimed:

1. A new and distinct cultivar of *Chionanthus* tree named 'CVJMW' as herein illustrated and described.

* * * * *